US012577292B2

(12) United States Patent
Kim et al.

(10) Patent No.: US 12,577,292 B2
(45) Date of Patent: Mar. 17, 2026

(54) FERRITIN NANOCAGE FOR MULTI-DISPLAYING TRAIL TRIMER AND CANCER-TARGETING PEPTIDE AND USE THEREOF AS ANTICANCER AGENT

(71) Applicant: KYUNGPOOK NATIONAL UNIVERSITY INDUSTRY-ACADEMIC COOPERATION FOUNDATION, Daegu (KR)

(72) Inventors: Soyoun Kim, Daegu (KR); Jae Do Yoo, Daegu (KR); Byung-Heon Lee, Daegu (KR); In Seon Jeon, Suncheon-si (KR); In-San Kim, Seoul (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 1000 days.

(21) Appl. No.: 17/436,070

(22) PCT Filed: Mar. 6, 2020

(86) PCT No.: PCT/KR2020/003166
§ 371 (c)(1),
(2) Date: Sep. 2, 2021

(87) PCT Pub. No.: WO2020/180144
PCT Pub. Date: Sep. 10, 2020

(65) Prior Publication Data
US 2022/0177547 A1    Jun. 9, 2022

(30) Foreign Application Priority Data

Mar. 7, 2019    (KR) ........................ 10-2019-0026274
Mar. 5, 2020    (KR) ........................ 10-2020-0027787

(51) Int. Cl.

| | |
|---|---|
| *C07K 14/79* | (2006.01) |
| *A61K 38/00* | (2006.01) |
| *A61P 35/00* | (2006.01) |
| *C07K 7/06* | (2006.01) |
| *C07K 14/705* | (2006.01) |

(52) U.S. Cl.
CPC .............. *C07K 14/79* (2013.01); *A61P 35/00* (2018.01); *C07K 7/06* (2013.01); *C07K 14/70575* (2013.01); *A61K 38/00* (2013.01); *C07K 2319/50* (2013.01)

(58) Field of Classification Search
CPC .... C07K 14/79; C07K 7/06; C07K 14/70575; C07K 2319/50; C07K 2319/00; C07K 14/70585; C07K 14/7155; A61P 35/00; A61K 38/00
See application file for complete search history.

(56) References Cited

U.S. PATENT DOCUMENTS

| | | | |
|---|---|---|---|
| 6,284,236 B1 | 9/2001 | Wiley et al. | |
| 8,461,311 B2 | 6/2013 | Hawkins et al. | |
| 9,403,892 B2 | 8/2016 | Zhou et al. | |
| 9,476,056 B2 | 10/2016 | Jan et al. | |
| 2004/0146968 A1* | 7/2004 | Chung ................. | C07K 14/705 |
| | | | 435/69.1 |
| 2016/0060307 A1* | 3/2016 | Jun .......................... | C07K 4/47 |

FOREIGN PATENT DOCUMENTS

| | | | | |
|---|---|---|---|---|
| KR | 10-2018-0008349 A | | 1/2018 | |
| WO | WO2009/007120 | * | 1/2009 | ........... C07K 14/525 |
| WO | WO 2018/053434 | * | 3/2018 | ............. A61K 47/64 |
| WO | WO2019172614 | * | 9/2019 | ............. A61K 38/00 |

OTHER PUBLICATIONS

English Translation of Kih WO2019172614 retrieved from PatentScope retrieved on Sep. 23, 2024 from https://patentscope.wipo.int/search/en/detail.jsf?docId=WO2019172614&_cid=P11-M1GDRP-72007-1 (Year: 2024).*
Steichen SD, Caldorera-Moore M, Peppas NA. A review of current nanoparticle and targeting moieties for the delivery of cancer therapeutics. Eur J Pharm Sci. Feb. 14, 2013;48(3):416-27. doi: 10.1016/j.ejps.2012.12.006. Epub Dec. 20, 2012. PMID: 23262059; PMCID: PMC3619023. (Year: 2013).*
Naeimi, R., Bahmani, A. & Afshar, S. Investigating the role of peptides in effective therapies against cancer. Cancer Cell Int 22, 139(2022). https://doi.org/10.1186/s12935-022-02553-7 (Year: 2022).*
NCBI accession No. P35247 retrieved on Nov. 7, 2024 from https://www.ncbi.nlm.nih.gov/protein/P35247/ (Year: 2024).*
Kim, S., Kim, G. S., Seo, J., Gowri Rangaswamy, G., So, I. S., Park, R. W., . . . & Kim, I. S. (2016). Double-chambered ferritin platform: dual-function payloads of cytotoxic peptides and fluorescent protein. Biomacromolecules, 17(1), 12-19. (Year: 2016).*
Yoo, J. D., Bae, S. M., Seo, J., Jeon, I. S., Vadevoo, S. M. P., Kim, S. Y., . . . & Kim, S. (2020). Designed ferritin nanocages displaying trimeric TRAIL and tumor-targeting peptides confer superior antitumor efficacy. Scientific reports, 10(1), 19997. (Year: 2020).*

(Continued)

*Primary Examiner* — Louise W Humphrey
*Assistant Examiner* — Kimberly Breen
(74) *Attorney, Agent, or Firm* — Revolution IP, PLLC

(57) ABSTRACT

A fusion nanoprotein is provided wherein TRAIL with a trimer structure is conjugated to a human ferritin monomer fragment and exhibits enhanced cancer targeting using a cancer-targeting peptide. The fusion protein effectively targets cancer cells when injected into a blood vessel, leading to TRAIL-induced cancer cell death. This fusion nanoprotein addresses key challenges of TRAIL proteins by improving their stability and reducing off-target effects through stable delivery of TRAIL trimers specifically to cancer tissues. The enhanced stability and targeted delivery properties make this fusion protein a promising candidate for development as an anticancer therapeutic agent.

3 Claims, 10 Drawing Sheets

Specification includes a Sequence Listing.

(56)         References Cited

OTHER PUBLICATIONS

Weiderpass, E. (2018). Cancer research for better public health policy—A personal view on the role of the International Agency for Research on Cancer in cancer control. Journal of cancer policy, 16, 70-72. (Year: 2018).*

"Preventable Cancers | the University of Kansas Cancer Center." The University of Kansas Cancer Center, 2021, www.kucancercenter.org/outreach/prevention/preventable-cancers. Accessed Nov. 7, 2024. (Year: 2021).*

Aden, D., Fogel, A., Plotkin, S. et al. Controlled synthesis of HBsAg in a differentiated human liver carcinoma-derived cell line. Nature 282, 615-616 (1979). https://doi.org/10.1038/282615a0 (Year: 1979).*

"CRI" Exploring the Different Types of Cancer and Treatment Options. (Dec. 12, 2023). Cancer Research Institute; CRI. https://www.cancerresearch.org/blog/exploring-the-different-types-of-cancer-and-treatment-options (Year: 2023).*

Deng, D., & Shah, K. (2020). TRAIL of hope meeting resistance in cancer. Trends in cancer, 6(12), 989-1001. (Year: 2020).*

International Search Report for PCT/KR2020/003166 mailed Jul. 30, 2020 from Korean Intellectual Property Office.

Quiang, P. L et al., "Engineering and refolding of a novel trimeric fusion protein TRAIL-collagen XVIII NC1", Applied Microbiology Biotechnology, 2013, vol. 97, pp. 7253-7264.

Xuechang Wu et al., "Trimeric coiled-coil domain of human pulmonary surfactant protein D enhances zinc-binding ability and biologic activity of soluble TRAIL", Molecular Immunology, vol. 46, 2009, pp. 2381-2388.

Minwoo Kih et al., "Designed trimer-mimetic TNF superfamily ligands on self-assembling nanocages", Biomaterials, vol. 180, 2018, pp. 67-77.

Kih Minwoo, "Designed trimer-mimetic TNF superfamily ligands on self-assembling nanocages", Thesis for the Degree of Master, Dec. 2017.

* cited by examiner

[FIG. 1]

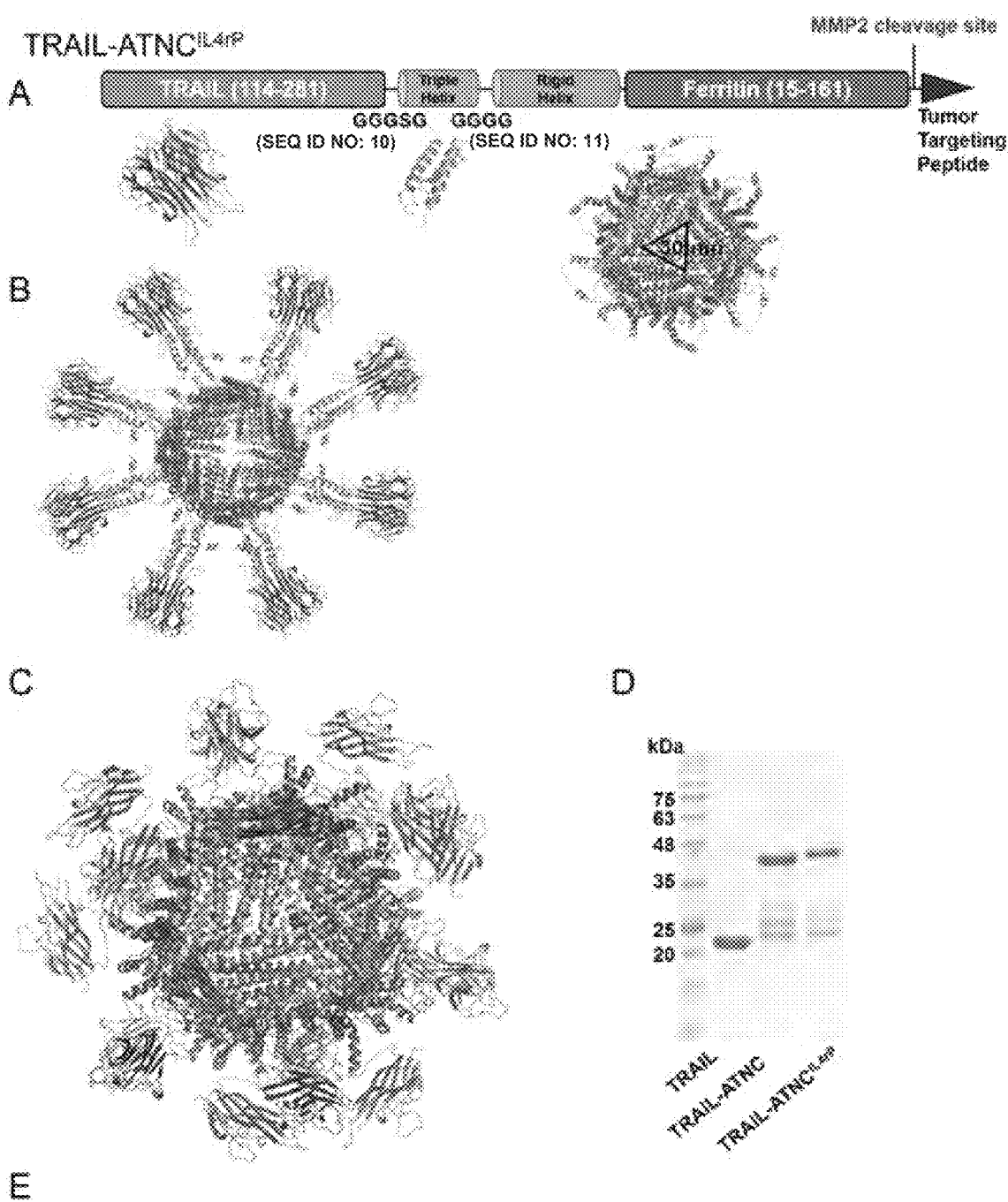

E

TRAIL-ATNC<sup>IL4rP</sup> amino acid sequence (IL. – Sffio. – CAA, Ndel. TRAIL, BamHI, GGGSG, EcoRI, Triple-helix, SalI, Rigid-helix, SpeI, sFTH, HindIII, GGGG, MBPC, GGGSG, IL4rP, TAA)

MGSSHHHHHHSSGLVPRGSQFMVREKGPQRVAAHITGTRGRSNTLSSPNSKNEKALGREINSWESSRSGHSFLSNLHLRN
GELVIHEKGFYYIYSQTYFRFQEEIKENTKNDKQMVQYIYKYTSYPDPILLMKSARNSCWSKDAEYGLYSIYQGGIFELKEND
RIPVSVTNEHLIDMDHEASFFGAFLVGQSTGGSEFDALQGGVQRLQAAPSQYKKVELFVDGGGGAEAAAKEAAAKTSDS
EAAINEQINLELYASYYLSMSTYFDRDDVALKNFAKYFLHQSHEEHEHAEKLMKLQNQRGGRIFLQDIKKFEDYESSEQL
NAMECALHLEEHVNQSLLELHKLATDKNDPHLCDFIETHYLNEQVKAIKELGDHVTNLRKMGAKLGGSNGSPLGLAGGGG
SGCRKKLDRNC (SEQ ID NO: 8)

[FIG. 2]
A
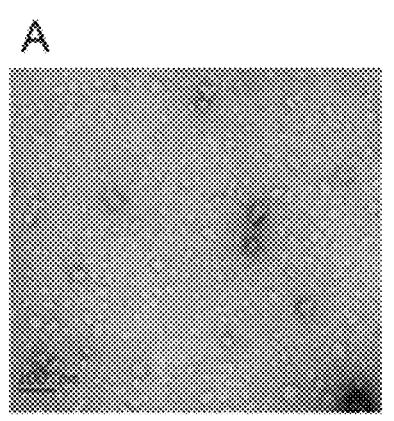
B
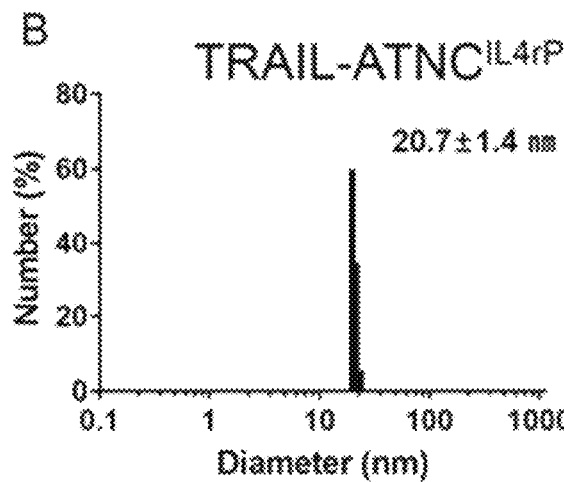
[FIG. 3]
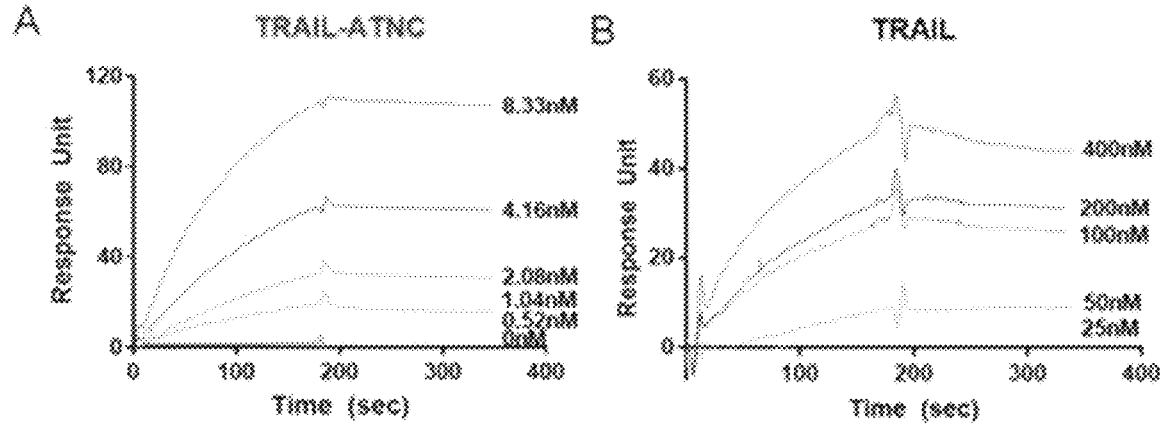

[FIG. 4]
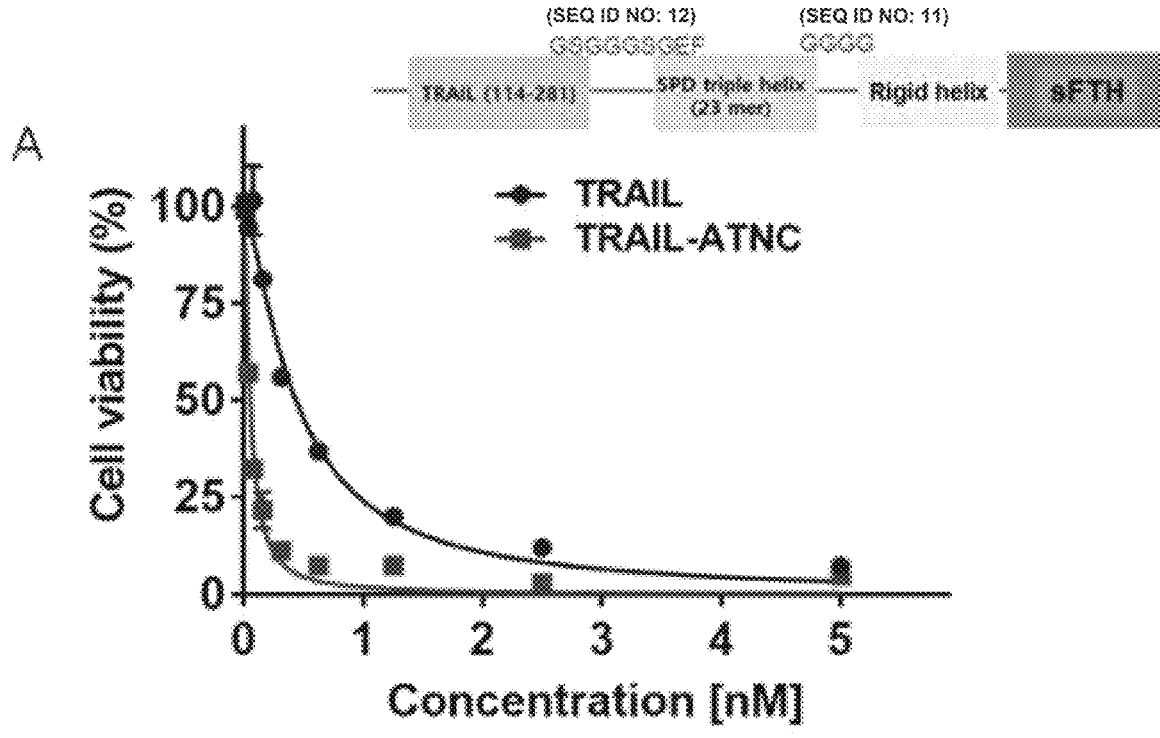
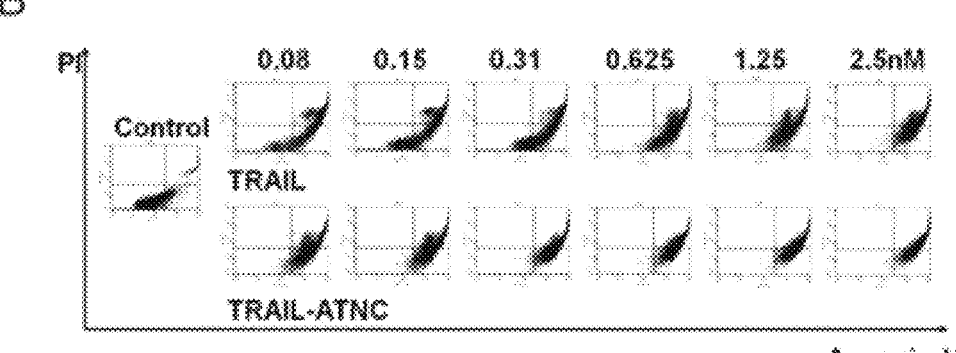

[FIG. 5]
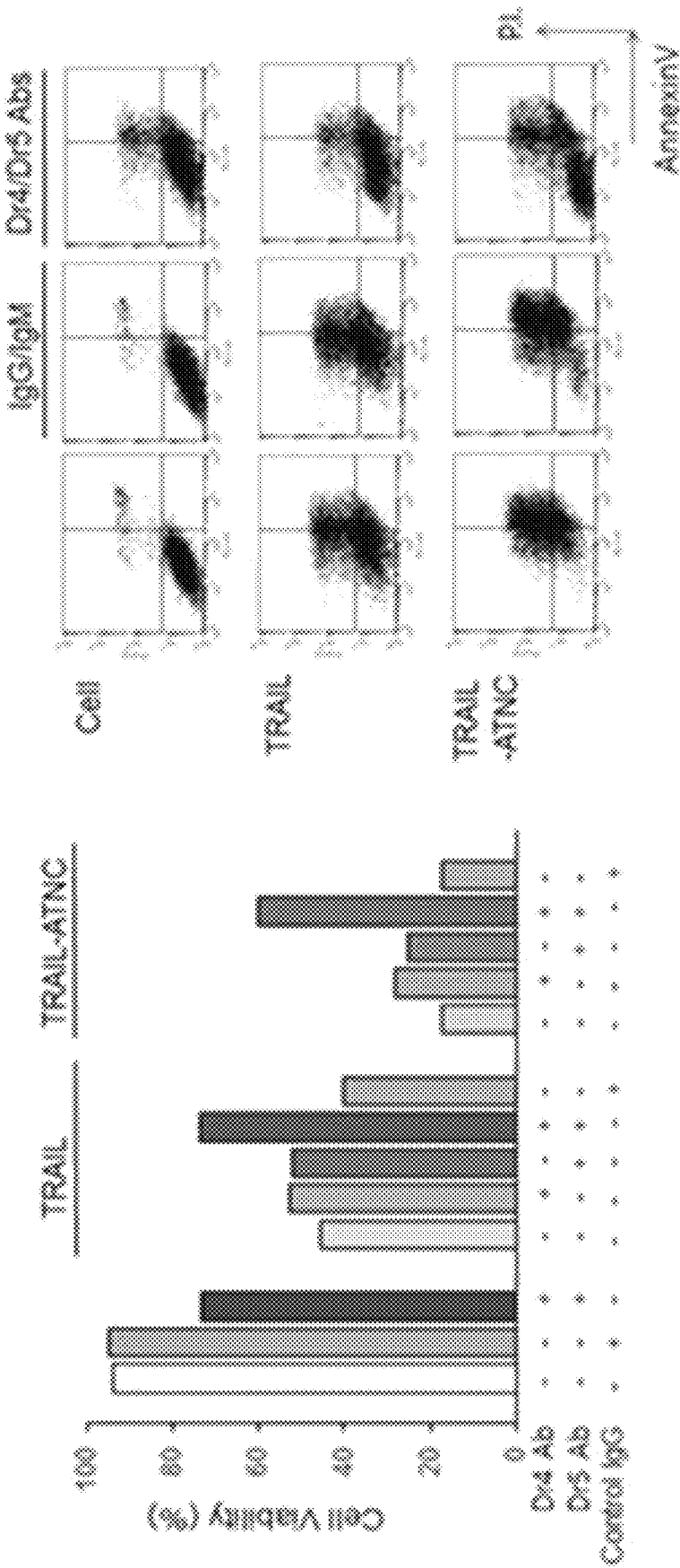

[FIG. 6]
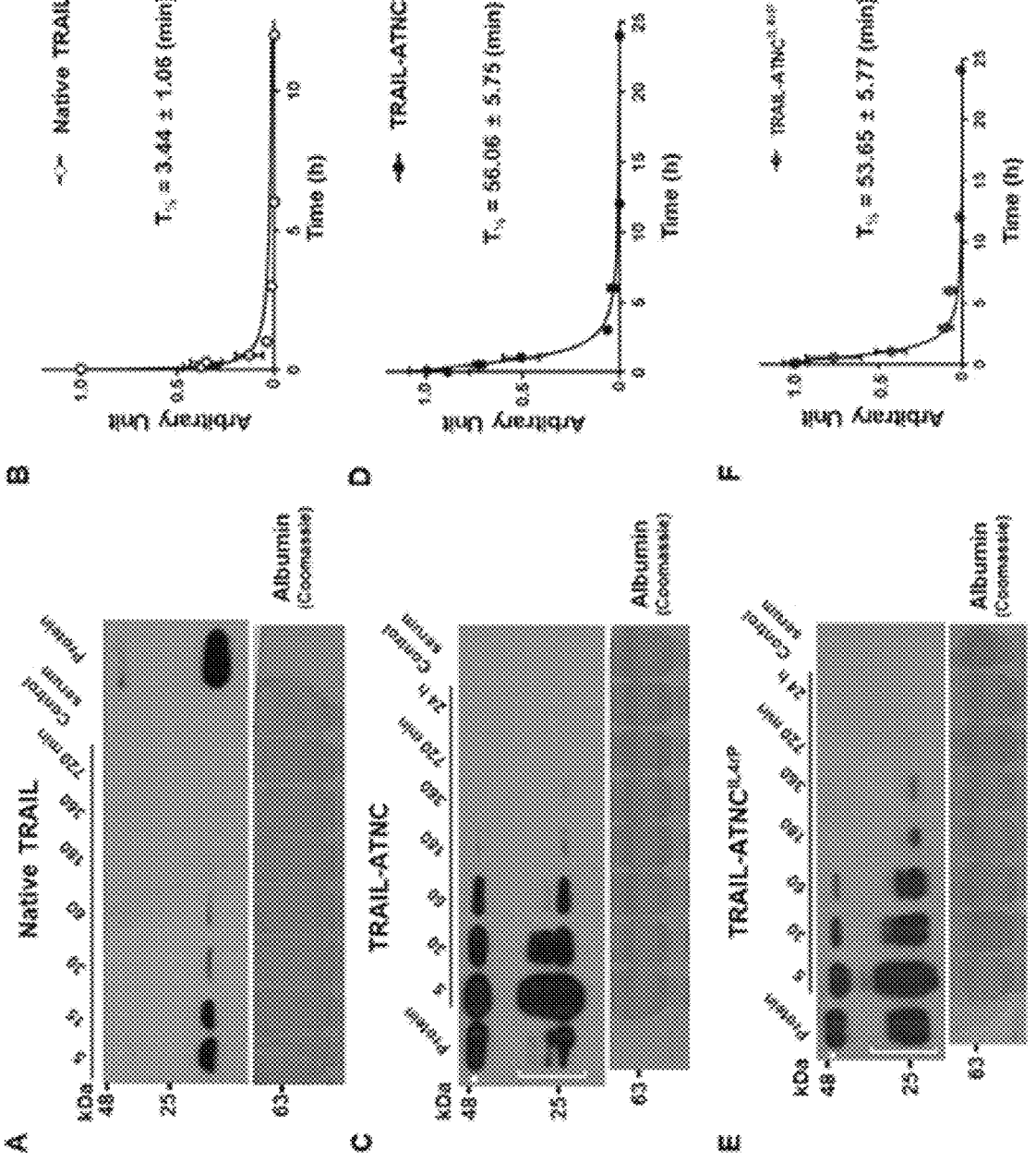

[FIG. 7]
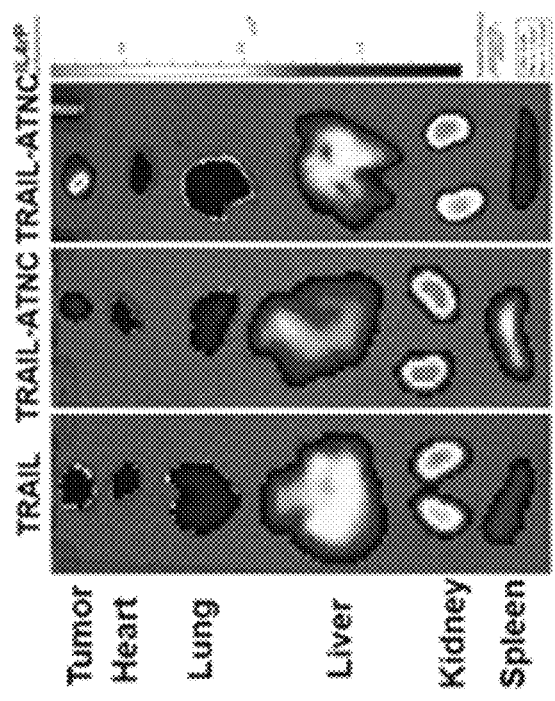
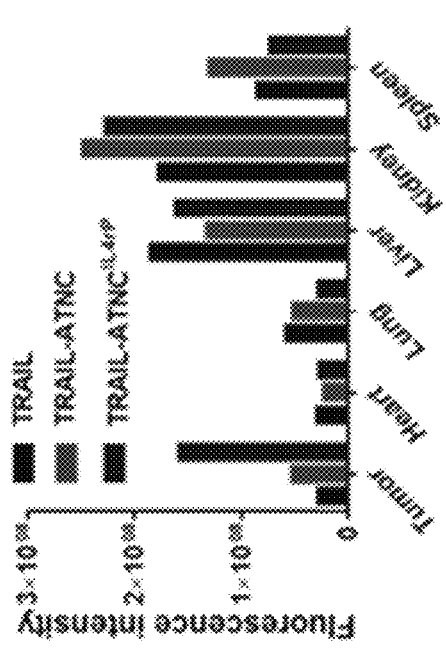
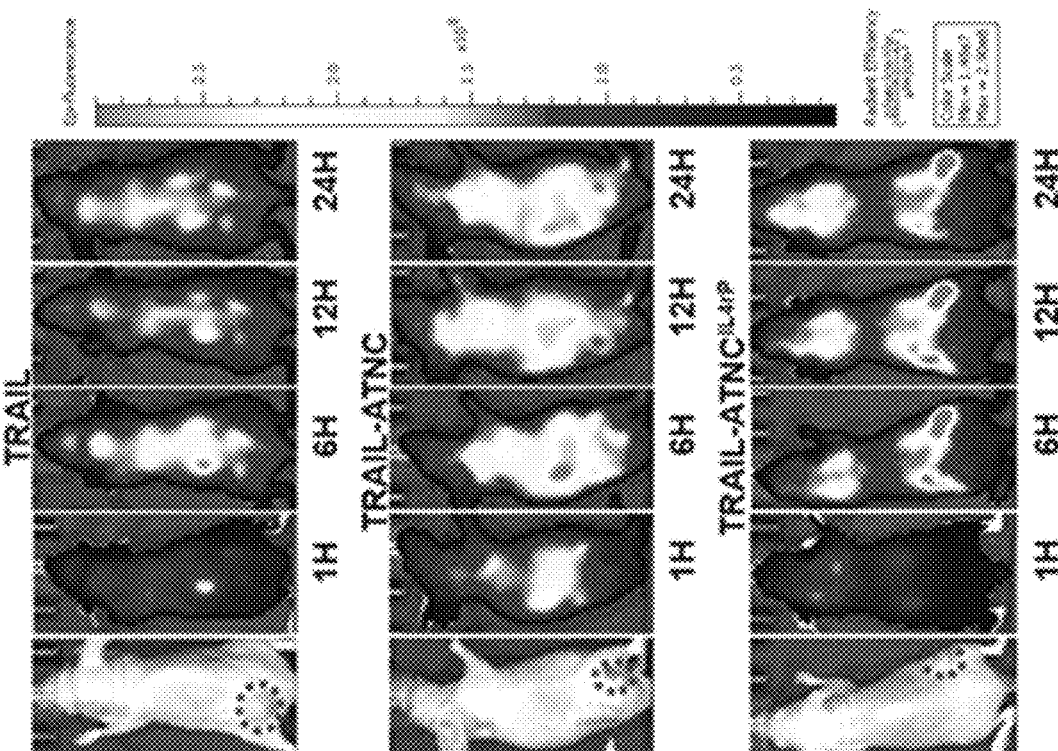

[FIG. 8]
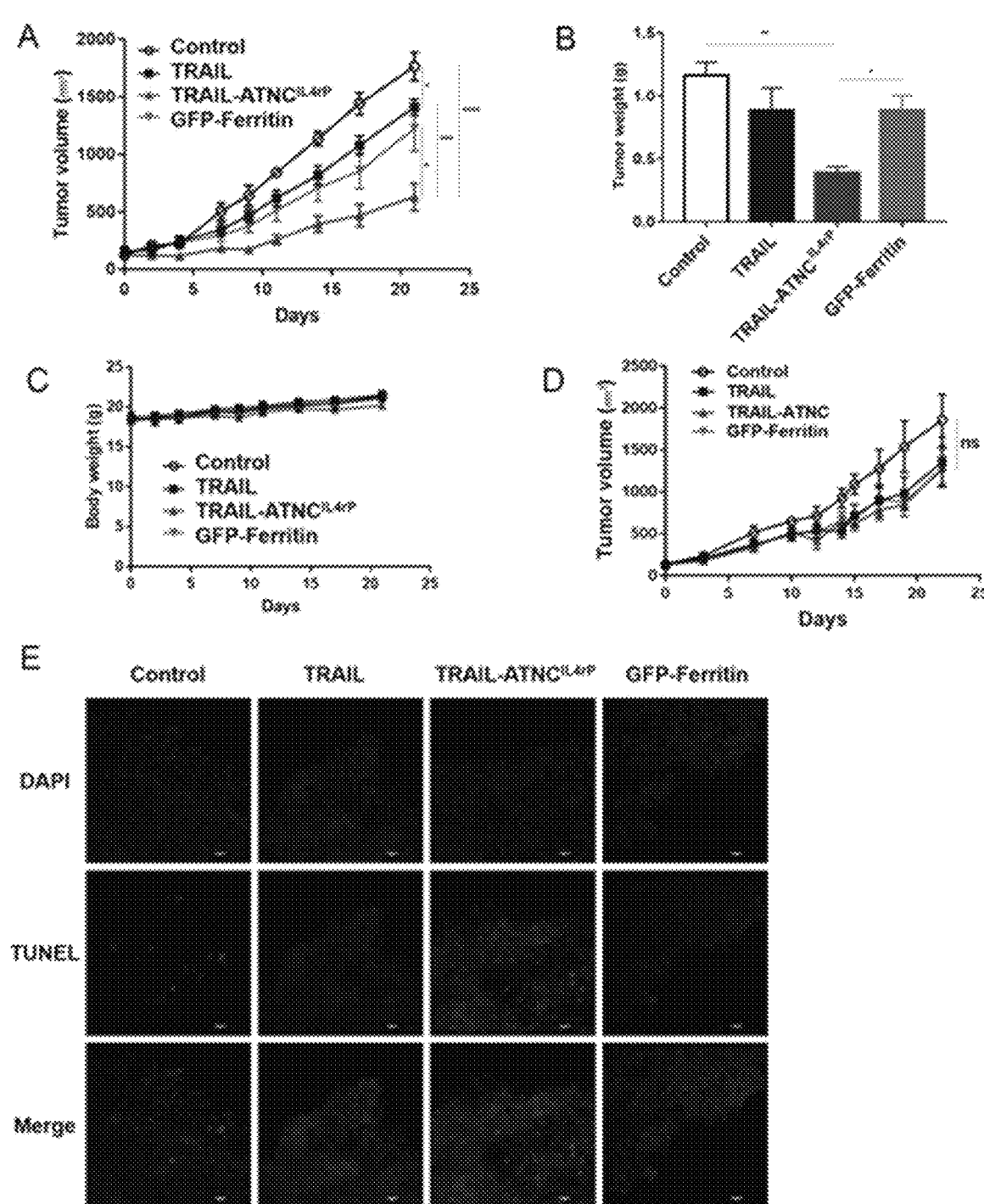

[FIG. 9]
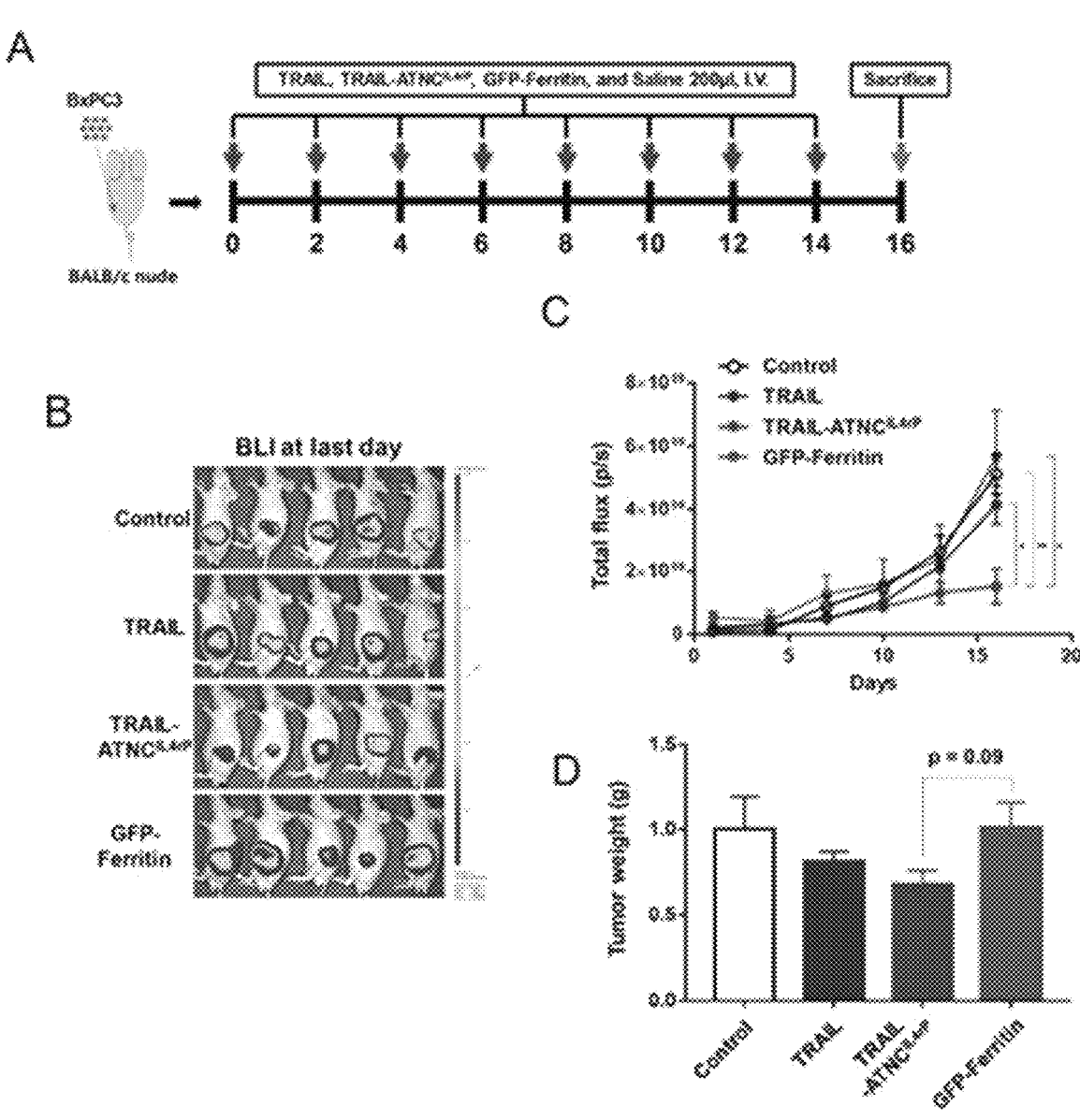

[FIG. 10]
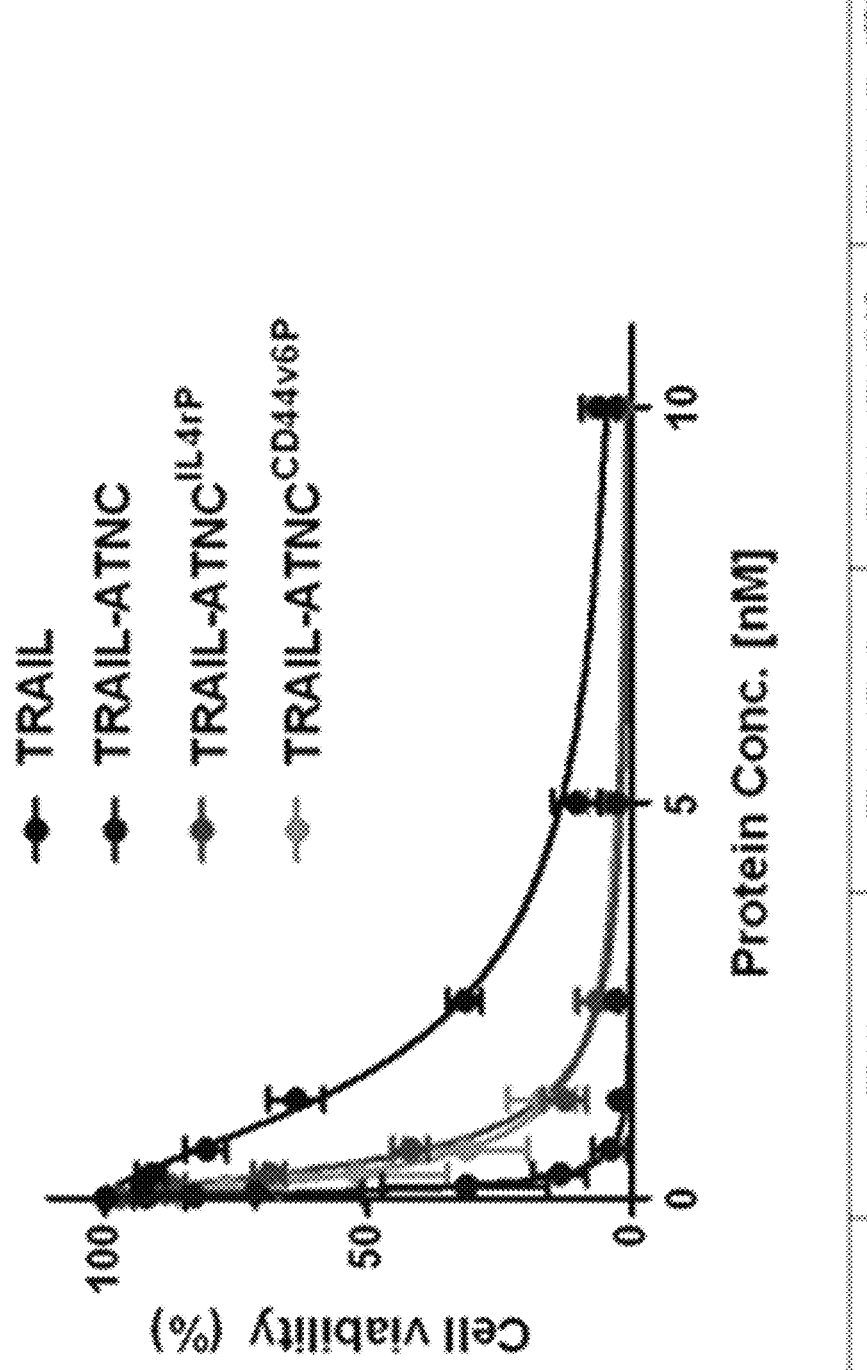

[FIG. 11]
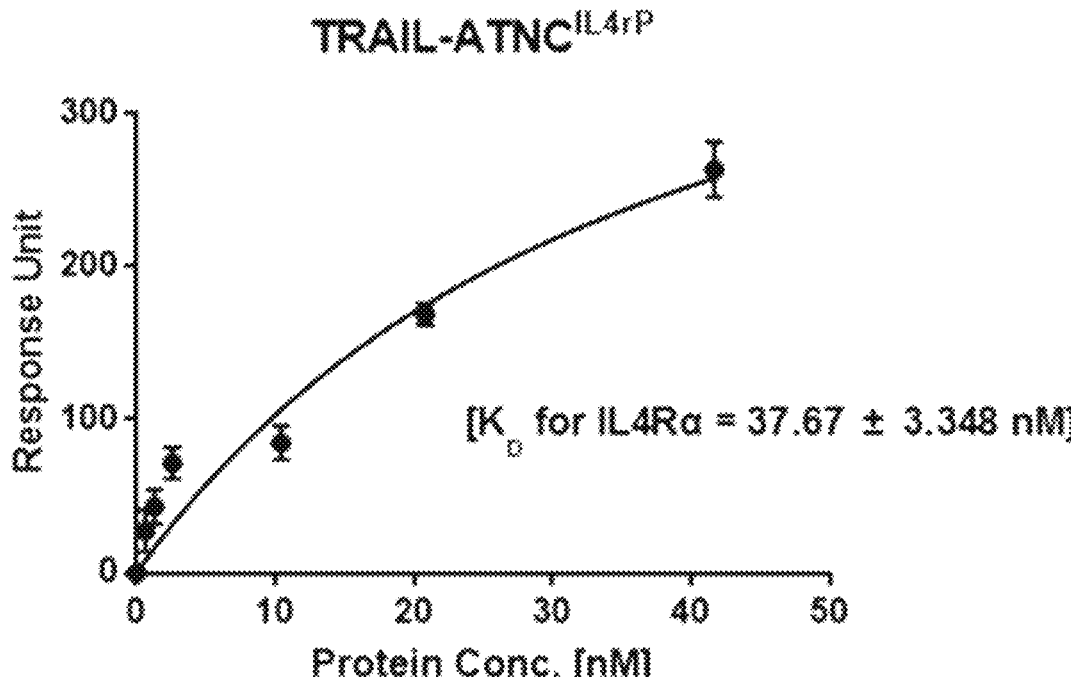
TRAIL-ATNC$^{IL4rP}$
[$K_D$ for IL4Rα = 37.67 ± 3.348 nM]

FERRITIN NANOCAGE FOR MULTI-DISPLAYING TRAIL TRIMER AND CANCER-TARGETING PEPTIDE AND USE THEREOF AS ANTICANCER AGENT

CROSS REFERENCE TO PRIOR APPLICATIONS

This application is the 35 U.S.C. 371 national stage of International application PCT/KR2020/003166 filed on Mar. 6, 2020; which claims priority to Korean Patent Application Nos. 10-2019-0026274 filed on Mar. 7, 2019 and 10-2020-0027787 filed on Mar. 5, 2020. The entire contents of each of the above-identified applications are hereby incorporated by reference.

TECHNICAL FIELD

The present invention relates to a ferritin nanocage for multi-displaying a trail trimer and a cancer-targeting peptide, and use thereof as an anticancer agent.

BACKGROUND ART

Cage protein is a protein capable of forming macromolecules tens to hundreds of times the molecular weight of a single-molecule due to a precise self-assembly property of low-molecular-weight monomolecules. In nature, viral capsid protein, ferritin, heat shock protein, and Dps protein are examples of the cage protein. The individual single molecules that compose a cage interact with their adjacent single molecules very precisely and regularly, and the inside of the cage is an empty structure. Since the inside and outside of the cage protein are isolated due to its container-like property as described above, it is frequently used as a drug carrier in the medical field.

In applications of material delivery using the cage protein, researches on viral and non-viral vectors are being actively conducted. Until now, adenoviruses and the like have been studied as the viral vectors, and ferritin, heat shock proteins and the like, have been studied as the non-viral vectors. However, in the case of the existing viral vector, an in-vivo safety issue has been raised due to genes within the virus itself.

Ferritin is a type of intracellular protein that stores and releases iron. Ferritin is generally in the form of a hollow spherical cage in vivo, and the cage is composed of 24 subunits, and the subunits are classified into a heavy chain and a light chain according to their structure.

On the other hand, TRAIL (TNF-related apoptosis inducing ligand) is a protein inducing apoptosis by binding to TRAIL receptor. TRAIL has proven superiority as an anticancer agent, but it is known that TRAIL specifically kills cancer cells by binding to a death receptor as a TRAIL trimer and is unstable and has little activity in binding to the death receptor as a TRAIL monomer. And, in clinical trials, its instability in blood and rapid exhaustion have been turned out to be problems.

Accordingly, it is necessary to develop a drug delivery platform that can solve the instability and off-targeting problem of the TRAIL protein itself developed as an anticancer effect protein, and stabilize TRAIL as an active trimer structure to effectively transport it to cancer tissues.

DISCLOSURE

Technical Problem

The present invention is objected to provide a fusion polypeptide including a human TRAIL fragment, a triple helix linker, a rigid helix linker, and a human ferritin heavy chain fragment, and a ferritin nanocage including the fusion polypeptide.

In addition, the present invention is objected to provide a fusion polypeptide including a human TRAIL fragment, a triple helix linker, a rigid helix linker, a human ferritin heavy chain fragment and a cancer-targeting peptide, and a ferritin nanocage including the fusion polypeptide.

In addition, the present invention is objected to provide a polynucleotide encoding the fusion polypeptide, an expression vector including the polynucleotide, and a transformant (except for humans) transformed with the expression vector.

In addition, the present invention is objected to provide a pharmaceutical composition for preventing or treating cancer including the fusion polypeptide as an active ingredient.

Technical Solution

In order to solve the above problems, the present invention provides a fusion polypeptide including a human TRAIL fragment consisting of an amino acid sequence represented by SEQ ID NO: 1, a triple helix linker, a rigid helix linker, and a human ferritin heavy chain fragment consisting of an amino acid sequence represented by SEQ ID NO: 2, and a ferritin nanocage comprising the fusion polypeptide.

In addition, the present invention provides a fusion polypeptide including a human TRAIL fragment comprising an amino acid sequence represented by SEQ ID NO: 1, a triple helix linker, a rigid helix linker, a human ferritin heavy chain fragment consisting of an amino acid sequence represented by SEQ ID NO: 2, and a cancer-targeting peptide, and a ferritin nanocage comprising the fusion polypeptide.

The present invention also provides a polynucleotide encoding the fusion polypeptide.

In addition, the present invention provides an expression vector comprising the polynucleotide.

In addition, the present invention provides a transformant (except for human) transformed with the expression vector.

In addition, the present invention provides a pharmaceutical composition for preventing or treating cancer including the fusion polypeptide as an active ingredient.

Advantageous Effects

The present invention relates to a ferritin nanocage for multi-displaying a TRAIL trimer and a cancer-targeting peptide, and use thereof as an anticancer agent, and relates to the development of a TRAIL fusion nanoprotein, in which TRAIL with a trimer structure is conjugated to a human ferritin monomer fragment, and which exhibits enhanced cancer targeting using a cancer-targeting peptide. When injected into a blood vessel, the fusion protein according to the present invention effectively targets cancer and thus effectively leads to cancer death caused by TRAIL. The fusion nanoprotein of the present invention, which addresses the instability and off-targeting problems of TRAIL proteins, stably delivers a TRAIL trimer to cancer tissue, and thus there is a high possibility of developing an anticancer agent using the same.

BRIEF DESCRIPTIONS OF DRAWINGS

FIG. 1 shows a TRAIL trimer fusion protein expressed on a cancer-targeting ferritin nanocage. A) A schematic diagram of the TRAIL trimer fusion protein (TRAIL-ATNC$^{IL4rP}$) expressed on the cancer-targeting ferritin nanocage according to the present invention is shown. B) A schematic diagram of an expected structure of TRAIL-ATNC$^{IL4rP}$ is shown. C) A result of computer simulation of the tertiary structure of TRAIL-ATNC$^{IL4rP}$ is shown. D) Results of SDS-polyacrylamide gel electrophoresis of TRAIL, TRAIL-ATNC, and TRAIL-ATNC$^{IL4rP}$ proteins are shown. E) An amino acid sequence of the TRAIL-ATNC$^{IL4rP}$ fusion protein is shown.

FIG. 2 shows results of purification and analysis of TRAIL-ATNC$^{IL4rP}$. A) A transmission electron microscope (TEM) analysis result of the purified TRAIL-ATNC$^{IL4rP}$ is shown. B) A result of dynamic light scattering (DLS) analysis of the purified TRAIL-ATNC$^{IL4rP}$ is shown.

FIG. 3 shows results of analysis of TRAIL receptor binding capacity for TRAIL-ATNC.

FIG. 4 shows analysis results for an apoptosis effect of TRAIL-ATNC. A) After treating MDA-MB-231 cells with TRAIL or TRAIL-ATNC, cell viability was measured using a cell number measurement kit (KLD-001, Rockland). B) It shows results of apoptosis according to TRAIL-ATNC treatment, measured by a cell flow rate analyzer.

FIG. 5 shows results of analyzing apoptosis of TRAIL and TRAIL-ATNC with or without DR4 antibody or DR5 antibody treatment.

FIG. 6 shows results of half-life analysis of TRAIL, TRAIL-ATNC, and TRAIL-ATNC$^{IL4rP}$ in the blood of mice. Protein: protein band of the same amount administered, Control serum: serum alone without protein administration, Albumin (coomassie): as an internal control, the presence of protein in the serum was checked through observation of albumin by coomassie blue staining.

FIG. 7 shows results of analysis of tumor targeting capability of TRAIL, TRAIL-ATNC, and TRAIL-ATNC$^{IL4rP}$.

FIGS. 8 and 9 show results of analysis of tumor suppressive effects of TRAIL, TRAIL-ATNC, and TRAIL-ATNC$^{IL4rP}$.

FIG. 10 shows results of apoptosis analysis of TRAIL-ATNC displaying a target peptide.

FIG. 11 shows results of analysis of targeting capability of a target peptide displayed on TRAIL-ATNC.

BEST MODE

The present invention provides a fusion polypeptide including a human TRAIL fragment consisting of an amino acid sequence represented by SEQ ID NO: 1, a triple helix linker, a rigid helix linker, and a human ferritin heavy chain fragment consisting of an amino acid sequence represented by SEQ ID NO: 2.

Preferably, the triple helix linker can be formed by inserting amino acid sequences at positions 233-255 among the protein sequences of pulmonary surfactant-associate protein D (human P35247) present in the human body, which are capable of forming a triple helix by themselves. More preferably, it may consist of the amino acid sequence represented by SEQ ID NO: 3 (EALQGQVQHLQAAF-SQYKKVELFP), but is not limited thereto.

Preferably, the rigid helix linker can use a sequence known to form a helical structure ordinarily. More preferably, it may consist of an amino acid sequence represented by SEQ ID NO: 4 (AEAAAKEAAAK), but is not limited thereto.

More preferably, the fusion polypeptide may consist of the amino acid sequence represented by SEQ ID NO: 5, but is not limited thereto.

In addition, the present invention provides a ferritin nanocage comprising the fusion polypeptide. More specifically, in the ferritin nanocage, TRAIL may be fused to the outer surface of the ferritin in the form of a trimer.

In addition, the present invention provides a fusion polypeptide including a human TRAIL fragment consisting of the amino acid sequence represented by SEQ ID NO: 1, a triple helix linker, a rigid helix linker, a human ferritin heavy chain fragment consisting of the amino acid sequence represented by SEQ ID NO: 2, and a cancer-targeting peptide.

Preferably, the fusion polypeptide may further include an MMP2 cleavage site between the human ferritin heavy chain fragment and the cancer targeting peptide. More preferably, the MMP2 cleavage site may consist of an amino acid sequence represented by SEQ ID NO: 7 (GPLGLAG), but is not limited thereto.

Preferably, the triple helix linker may be formed by inserting amino acid sequences at positions 233-255 among the protein sequences of pulmonary surfactant-associate protein D (human P35247) present in the human body, which are capable of forming a triple helix by themselves. More preferably, it may consist of the amino acid sequence represented by SEQ ID NO: 3 (EALQGQVQHLQAAF-SQYKKVELFP), but is not limited thereto.

Preferably, the rigid helix linker can uses a sequence known to form a helical structure ordinarily, and more preferably consist of the amino acid sequence represented by SEQ ID NO: 4 (AEAAAKEAAAK). However, the present invention is not limited thereto.

Preferably, the cancer-targeting peptide may be an interleukin 4 receptor binding peptide (IL4rP) or a CD44 binding peptide (CD44v6P). More preferably, the interleukin 4 receptor binding peptide (IL4rP) consists of an amino acid represented by SEQ ID NO: 6 (CRKRLDRNC), and the CD44 binding peptide (CD44v6P) may consist of an amino acid sequence represented by SEQ ID NO: 9 (CNLN-TIDTC). The present invention is not limited thereto.

More preferably, the fusion polypeptide may consist of an amino acid sequence represented by SEQ ID NO: 8, but is not limited thereto.

In addition, the present invention provides a ferritin nanocage including the fusion polypeptide. In detail, in the ferritin nanocage, TRAIL may be fused to the outer surface of the ferritin in the form of a trimer, and a cancer-targeting peptide may protrude out of the ferritin nanocage.

In the present invention, the human TRAIL fragment (114-281) consisting of the amino acid sequence represented by SEQ ID NO: 1 includes a TRAIL receptor binding domain.

In the present invention, the 'ferritin' is a kind of intracellular protein and serves to store and release iron. Ferritin is generally in the form of a hollow spherical cage in vivo, the cage consists of 24 ferritin monomers, and the ferritin monomer is divided into a heavy chain and a light chain depending on its structure. In the present invention, the ferritin proteins may be used without limitation as long as each of the proteins has an activity capable of forming a cage-type complex protein as a unit.

In the present invention, in order to help maintain the triple structure of TRAIL, a human ferritin heavy chain fragment (15-161) consisting of the amino acid sequence represented by SEQ ID NO: 2, in which the 14 amino acid sequences at the ferritin N-terminus were deleted, was used.

In the present invention, the "nanocage" is a cage made of protein, which is formed by the precise self-assembly of low molecular weight monomers, and has a space therein. These include viral capsid protein, ferritin, heat shock protein, and Dps protein. The nanocage of the present invention is characterized by including the fusion polypeptide of the present invention as monomers that form the nanocage. As used herein, the term "self-assembly" refers to the property that certain molecules form a specific nano-structure on their own without special external stimulation or artificial induction.

The nanocage of the present invention may be a complex protein in which the fusion polypeptide of the present invention is regularly arranged as a unit. More preferably, it may be formed by regularly arranging 24 fusion polypeptides of the present invention in three dimensions.

The present invention also provides a polynucleotide encoding the fusion polypeptide.

The "polynucleotide" is a polymer of deoxyribonucleotides or ribonucleotides that exist in a single-stranded or double-stranded form. It encompasses RNA genomic sequences, DNA (gDNA and cDNA) and RNA sequences transcribed therefrom, and includes analogs of natural polynucleotides unless otherwise specified.

The polynucleotide includes not only the nucleotide sequence encoding the fusion polypeptide, but also a sequence complementary to the sequence. The complementary sequence includes not only a perfectly complementary sequence, but also a substantially complementary sequence.

In addition, the polynucleotide may be modified. Such modifications include additions, deletions, or non-conservative substitutions or conservative substitutions of nucleotides. The polynucleotide encoding the amino acid sequence is construed to include a nucleotide sequence exhibiting substantial identity to the nucleotide sequence. The substantial identity aligns the nucleotide sequence and any other sequence so that they correspond as much as possible. When analyzed using an algorithm commonly used in the art, the aligned sequences may show at least 80% homology, at least 90% homology, or at least 95% homology.

In addition, the present invention provides an expression vector including the polynucleotide.

In addition, the present invention provides a transformant (except for human) transformed with the expression vector.

In the present invention, "vector" refers to a self-replicating DNA molecule used to carry a clonal gene (or another piece of clonal DNA).

In the present invention, the "vector" refers to a plasmid, a viral vector or other vehicles known in the art capable of expressing an inserted nucleic acid in a host cell, and the polynucleotide encoding the fusion polypeptide of the present invention may be operably linked with a conventional expression vector known in the art. The expression vector includes generally an origin of replication capable of proliferation in a host cell, one or more expression control sequences regulating expression (e.g., promoter, enhancer, etc.), a selective marker, and the polynucleotide encoding the fusion polypeptides of the invention operably linked to an expression control sequence. The transformant may be transformed by the expression vector.

Preferably, the transformant can be obtained by introduction of the expression vector including the polynucleotide encoding the fusion polypeptide of the present invention into the host cell by a method known in the art including, but not limited to, transient transfection, microinjection, transduction, cell fusion, calcium phosphate precipitation, liposome-mediated transfection, DEAE Dextran-mediated transfection, polybrene-mediated transfection, electroporation, gene gun, and other known methods for introducing nucleic acids into cells.

In addition, the present invention provides a pharmaceutical composition for preventing or treating cancer including the fusion polypeptide as an active ingredient.

Preferably, the cancer may be lung cancer, brain tumor, breast cancer, liver cancer, skin cancer, esophageal cancer, testicular cancer, kidney cancer, colorectal cancer, rectal cancer, stomach cancer, bladder cancer, ovarian cancer, bile duct cancer, gallbladder cancer, uterine cancer, cervical cancer, prostate cancer, head and neck cancer, pancreatic cancer, or squamous cell carcinoma, but is not limited thereto.

The pharmaceutical composition of the present invention may be prepared using a pharmaceutically suitable and physiologically acceptable adjuvant in addition to the active ingredient, and the adjuvant includes an excipient, a disintegrant, a sweetener, a binder, a coating agent, a blowing agent, a lubricant, a slip modifier, a flavoring agent, or a solubilizing agent. The pharmaceutical composition of the present invention may be preferably formulated into a pharmaceutical composition including one or more pharmaceutically acceptable carriers in addition to the active ingredient for administration. In the composition formulated as a liquid solution, acceptable pharmaceutical carriers are sterile and biocompatible, and may include saline, sterile water, Ringer's solution, buffered saline, albumin injection, dextrose solution, maltodextrin solution, glycerol, ethanol, and any combination thereof. Further, other conventional additives such as antioxidants, buffers, and bacteriostatic agents may be added as needed. In addition, diluents, dispersants, surfactants, binders, and/or lubricants may be additionally added to form an injectable formulation such as an aqueous solution, suspension, emulsion, etc., pills, capsules, granules, or tablets.

The pharmaceutical formulation of the pharmaceutical composition of the present invention may be granules, powders, coated tablets, tablets, capsules, suppositories, syrups, juices, suspensions, emulsions, drops, injectable solutions, or sustained-release formulations of the active compound. The pharmaceutical composition of the present invention may be administered in a conventional manner via intravenous, intraarterial, intraperitoneal, intramuscular, intraarterial, intraperitoneal, intrasternal, transdermal, intranasal, inhalational, topical, rectal, oral, intraocular, or intradermal routes. An effective amount of the active ingredient of the pharmaceutical composition of the present invention means the amount required for prevention or treatment of a disease. Therefore, it can be adjusted according to various factors including the type of disease, the severity of the disease, the type and content of the active ingredient and other ingredients contained in the composition, the type of dosage form and the age, weight, general health status, sex and diet of the patient, administration time, administration route, secretion rate of the composition, duration of treatment, and drugs used at the same time. For example, in the case of an adult, when administered once to several times a day, the composition of the present invention can be administered at a dose of 0.1 ng/kg to 10 g/kg, but the present invention is not limited thereto.

MODES FOR CARRYING OUT INVENTION

Hereinafter, the present invention will be described in detail through the examples that do not limit the present invention. Of course, the following examples of the present invention are only for specifying the present invention, but are not intended to limit or restrict the scope of the present invention. Accordingly, what can be easily inferred by an expert in the technical field from the detailed description and examples of the present invention, is construed as being included in the scope of claims in the present invention.

Experimental Example

The following experimental examples are intended to provide experimental examples commonly applied to each embodiment according to the present invention.
1. TRAIL-ATNC$^{IL4rP}$ DNA Production
   Human TRAIL (114-281), a triple helix gene, a rigid helix gene, a human ferritin heavy chain (15-161) gene, an MMP2 cleavage site gene, and a gene sequence of the peptide binding to the interleukin 4 receptor, were inserted into pET-28a plasmid according to a genetic recombination method. To increase the degree of freedom, a gene encoding GGGSG (SEQ ID NO: 10) was inserted between the TRAIL (114-281) and the triple helix gene, and a gene encoding GGGG (SEQ ID NO: 11) was inserted between the triple helix and the rigid helix genes. The human ferritin heavy chain gene and the human TRAIL gene were obtained by PCR amplification using primers of each gene from a cDNA library reverse transcribed from human mRNA. Other genes were chemically synthesized and used.
2. Purification of TRAIL-ATNC$^{IL4rP}$ and TRAIL-ATNC Proteins
   E. coli (BL21) transformed with the plasmid into which the TRAIL-ATNC$^{IL4rP}$ sequence was inserted, was inoculated into LB medium and grown in a shaker incubator at 37° C. When the OD$_{600}$ value reached 0.5, IPTG was added to the medium to 100 uM and the protein overexpression was induced. After IPTG was added, it was grown overnight in the shaker incubator at 18° C., and only E. coli was collected by centrifugation. E. coli which lysis buffer was added to, was pulverized by ultrasonication. The supernatant (lysate) collected by centrifugation was mixed with Ni-NTA beads for 1 hour. The lysate that was not bound to the beads was discarded by the chromatography column, and the beads were washed with a wash buffer containing 30 mM imidazole. E. coli endotoxin was removed with a wash buffer containing 0.1% Triton X-114, and TritonX-114 was removed with a wash buffer. Proteins were eluted and purified using an elution buffer containing 100 mM, 200 mM, and 300 mM of imidazole. More than 95% homogeneous purified protein was recovered by SDS PAGE.

<Example 1> TRAIL Trimer Expressed on Cancer-Targeted Ferritin Nanocages

Human TRAIL (114-281) having a TRAIL receptor binding domain was combined genetically with the N-terminus of the human ferritin heavy chain fragment (15-161), and a linker was attached between TRAIL and the ferritin. At this time, in order to help maintain the triple structure of TRAIL, a rigid helix structure is established at the triple junction at a distance of about 30 Å by deleting the 14 amino acid sequences at the ferritin N-terminus, a triple helix having a property to from a triple helix on its own was inserted on it, and then TRAIL (114-281) was inserted. A degree of freedom was imposed by inserting a flexible linker such as GGGSG (SEQ ID NO: 10) between the helix and the protein domain. This was named TRAIL-ATNC (Active Trimer Nanocage).

Since the carbon terminus of the ferritin in which the fifth helix had been removed was exposed to the outside, a peptide (IL4rP) binding to the interleukin 4 receptor was bound to this position so that the ferritin nanocage had tumor-targeting capability in vivo. By inserting a sequence cut by MMP2 enzyme therebetween, the ferritin nanocage binds to the interleukin 4 receptor in the vicinity of the tumor, and then the ferritin nanocage which was freed by cleavage can also bind to the TRAIL receptor. Due to this design, the action of the ferritin is not inhibited by the targeting peptide. TRAIL-ATNC to which the peptide was attached was named TRAIL-ATNC$^{IL4rP}$ (FIG. 1A). On the other hand, a schematic diagram of an expected structure of TRAIL-ATNC$^{IL4rP}$ is shown in FIG. 1B.

In addition, as a result of computer simulation of the tertiary structure of TRAIL-ATNC$^{IL4rP}$, it was predicted that TRAIL could be folded into a multimer outside of the ferritin. At this time, MODELLAR v12 was used as a modeling program (FIG. 1C).

When electrophoresis of TRAIL, TRAIL-ATNC, TRAIL-ATNC$^{IL4rP}$ proteins was performed by SDS-polyacrylamide gel electrophoresis, and protein bands were observed by staining the gel with Coomassie Brilliant Blue, stable expression and purification in Escherichia coli were verified by identifying the protein band at the same position with the theoretical monomer size of each protein. In the case of TRAIL-ATNC and TRAIL-ATNC$^{IL4rP}$ about 1-2 mg of purified protein was stably recovered when 1 L of E. coli was cultured. In addition, there was no significant difference between TRAIL-ATNC and TRAIL-ATNC$^{IL4rP}$ in in vitro tests for binding to TRAIL receptor (DR5) or apoptosis of cancer cells (FIG. 1D).

<Example 2> Purification and Analysis of TRAIL-ATNC$^{IL4rP}$

TRAIL-ATNC$^{IL4rP}$ was purified from E. coli overexpressing TRAIL-ATNC using Ni-NTA beads. Transmission electron microscopy (TEM) analysis was performed to determine whether or not the purified protein formed a ferritin nanocage, and it was determined that TRAIL-ATNC$^{IL4rP}$ formed a nanocage (FIG. 2A). Further, by performing dynamic light scattering (DLS) analysis, it was determined that the size of TRAIL-ATNC$^{IL4rP}$ was about 21 nm (FIG. 2B).

<Example 3> TRAIL Receptor Binding Capacity Analysis for TRAIL-ATNC

The TRAIL receptor protein Dr5 was coupled to a surface of a gold sensor chip by flowing it on the surface of the gold sensor chip for surface resonance plasma (SPR) activated with NHS-EDC, and blocked with ethanolamine. The binding kinetics were analyzed by flowing TRAIL-ATNC dissolved in TBS from 8.33 nM to 0.52 nM by half, and TRAIL from 400 nM to 25 nM by half on the TRAIL receptor-coupled gold sensor chip, respectively. The right channel, which was not coated with Dr5, was used as a control (or reference).

TRAIL-attached nanocage TRAIL-ATNC showed about 10-fold higher $k_{on}$ and 10-fold lower $k_{off}$ values than TRAIL alone. It was determined that TRAIL-ATNC bound to the TRAIL receptor faster than TRAIL, and formed a stable complex in which dissociation was delayed after binding. The overall dissociation constant ($K_D$) value of TRAIL-ATNC was about 100-fold lower than that of TRAIL, indicating that the binding capacity of TRAIL-ATNC to the TRAIL receptor was increased by about 100-fold compared to TRAIL (FIG. 3 and Table 1).

TABLE 1

| | $k_{on}$ ($M^{-1}S^{-1}$) | $k_{off}$ ($S^{-1}$) | $K_D$ (M) |
|---|---|---|---|
| TRAIL | $2.57 \times 10^4$ | $1.50 \times 10^{-3}$ | $58.26 \times 10^{-9}$ |
| TRAIL-ATNC | $5.29 \times 10^5$ | $2.17 \times 10^{-4}$ | $41.07 \times 10^{-11}$ |

<Example 4> Cell Death Analysis According to TRAIL and TRAIL-ATNC Treatment

MDA-MB-231 cells were seeded in each well of a 96-well plate by $5 \times 10^3$ cells and cultured in DMEM medium (2% FBS) at 37° C. After 24 hours, the protein of each of TRAIL and TRAIL-ATNC dissolved in modified PBS (500 mM NaCl, 1 mM DTT) was treated to cells from 5 nM to 0.04 nM by half and then cultured at 37° C. for 24 hours again. Thereafter, cell viability was measured using a cell number measurement kit (KLD-001, Rockland). At this time, relative cell viability was measured when the non-protein-treated cell group was set to 100% as a control.

Compared to TRAIL, TRAIL-ATNC ($IC^{50}$=0.05 nM), in which TRAIL is displayed outside the ferritin nanocage, showed 10-fold higher cytotoxicity than TRAIL ($IC^{50}$=0.4 nM) (FIG. 4A).

In addition, an enhancing effect of TRAIL-ATNC apoptosis was verified again by measuring the phosphatidylserine exposed to the outer cell membrane during cell death with a cell flow rate analyzer by staining the cells with Annexin V-FITC and Propidium Iodide (FIG. 4B).

<Example 5> Cell Death Analysis of TRAIL and TRAIL-ATNC with or without DR4 Antibody or DR5 Antibody Treatment MDA-MB-231 cells were seeded in each well of a 6-well plate (35 mm) by $1 \times 10^5$ cells and cultured at 37° C. After 24 hours, cells were treated with DR4 antibody (200 ng/ml), DR5 antibody (5 μg/ml), or a control antibody, respectively, or simultaneously. After cultivation at 37° C. for 1 hour, the cells were treated with 2.5 nM or 0.3 nM of the protein of each of TRAIL and TRAIL-ATNC dissolved in modified PBS (500 mM NaCl, 1 mM DTT) and cultured at 37° C. for 3 hours. The cells were detached with trypsin and stained with Annexin V-FITC and Propidium Iodide, and the level of cell death was analyzed by a cytometry.

Apoptosis by TRAIL and TRAIL-ATNC treatment was not inhibited when the DR4 antibody or DR5 antibody was treated, respectively, but in the group treated with both antibodies, apoptosis by TRAIL or TRAIL-ATNC was inhibited. Through this result, it was determined that TRAIL-ATNC, like TRAIL, also induces apoptosis by specific binding to DR4 and DR5 (FIG. 5).

<Example 6> Analysis of Half-Life of TRAIL, TRAIL-ATNC and TRAIL-ATNC$^{IL4rP}$ in Blood of Mice 200 μl of each of native TRAIL (10 μg/ml), TRAIL-ATNC (1.0 mg/ml) and TRAIL-ATNC$^{IL4rP}$ (1.0 mg/ml) proteins dissolved in saline were injected into the ophthalmic venous sinus of each BALB/c wild-type mouse. Blood was collected after 5 minutes, 15 minutes, 30 minutes, 1 hour, 3 hours, 6 hours, 12 hours, and 24 hours from injection. Blood in mice injected with the same amount of saline alone into the ophthalmic venous sinus was collected 24 hours later. Serum was obtained from the blood and fractionated with SDS, and then Western blot was performed using the TRAIL antibody.

In mice treated with saline only (serum only), no band responding to the TRAIL antibody was detected, so in comparison of size, it is construed that the protein shown is the protein (TRAIL, TRAIL-ATNC, or TRAIL-ATNC$^{IL4rP}$) or its degraded products. The half-lives of TRAIL, TRAIL-ATNC and TRAIL-ATNC$^{IL4rP}$ were calculated based on the thickness of the protein band detected for each time.

As a result, the half-life of TRAIL in the blood of mice was about 3.5 minutes, but the half-lives of TRAIL-ATNC and TRAIL-ATNC$^{IL4rP}$ were about 56 minutes and 53 minutes, respectively, showing stability that increased more than 15 times. According to the literature, the half-life of TRAIL-only protein in rodents is 3-5 minutes, and the half-life in humans is about 30 minutes. Therefore, the half-life of TRAIL-ATNC and TRAIL-ATNC$^{IL4rP}$ in the human body is also expected to increase. After 24 hours, TRAIL, TRAIL-ATNC and TRAIL-ATNC$^{IL4rP}$ all completely disappeared from the blood. Protein is a band of the same amount of protein administered, and control serum is serum alone to which no protein is administered. Albumin (coomassie) was identified as an internal control through coomassie blue staining of albumin to identify the presence of proteins in the serum.

<Example 7> Analysis of Tumor Targeting Capability of TRAIL, TRAIL-ATNC and TRAIL-ATNC$^{IL4rP}$ $1 \times 10^6$ MDA-MB-231 cells in 100 μl of PBS were subcutaneously injected into the right thigh of 6-week-old BALB/c immunodeficient mice. When the size of the tumor was about 100 mm$^3$, 200 μl of TRAIL (0.5 mg/ml), TRAIL-ATNC (1.0 mg/ml), and TRAIL-ATNC$^{IL4rP}$ (1.0 mg/ml) proteins dissolved in saline and labeled with FPI-774, respectively, were injected into the tail vein of each mouse.

The biodistribution of proteins at 1 hour, 6 hours, 12 hours, and 24 hours after injection was investigated using the IVIS fluorescence imaging system. After 24 hours, mice were sacrificed, and tumors, heart, lung, liver, kidney, and spleen were taken out to examine how much protein remained in the organs.

In the case of TRAIL and TRAIL-ATNC proteins, they had no tumor-targeting capability and were observed to accumulate in the kidney. TRAIL-ATNC increased in vivo tumor targeting capability compared to TRAIL by EPR effect, but there was no significant difference. However, it was found that the in vivo tumor targeting capability of TRAIL-ATNC$^{IL4rP}$ to which a target peptide (IL4R-binding peptide: IL4rP) was added significantly increased compared to that of TRAIL and TRAIL-ATNC (FIG. 7).

<Example 8> Analysis of Tumor Suppression Effect of TRAIL, TRAIL-ATNC and TRAIL-ATNC$^{IL4rP}$ $3 \times 10^6$ MDA-MB-231 cells in 100 μl of PBS were subcutaneously injected into the right thigh of 6-week-old BALB/c immunodeficient mice. When the size of the tumor was about 100 mm$^3$, they were randomly divided into 4 groups. For each group, one of saline, and TRAIL (0.5 mg/ml), TRAIL-ATNC$^{IL4rP}$ (1.0 mg/ml), and Ferritin (1.0 mg/ml) proteins dissolved in saline was injected into the tail vein of each mouse at 200 μl. The size of the tumor and the weight of the mice were measured while injecting 3 times a week for a total of 8 times. When measuring the anticancer effect as described above, 200 µl of each of saline and TRAIL (0.5 mg/ml), TRAIL-ATNC (1.0 mg/ml), and Ferritin (1.0 mg/ml) proteins dissolved in saline, was injected into the tail vein of each mouse in each group randomly divided. After 3 weeks, some of the mice were sacrificed, the tumor was harvested, and the weight of the tumor was measured. In addition, the harvested tumor was sliced to make a thin slide, and TUNEL assay was performed.

As a result, tumor growth was significantly inhibited by TRAIL alone ($p<0.05$) compared to the control group. TRAIL-ATNC$^{IL4rP}$ significantly inhibited the growth of the tumor compared to not only the control group ($p<0.0001$), but also to TRAIL ($p<0.001$) (FIG. 8A), and the weight of the tumor was much smaller (FIG. 8B). Further, TRAIL-ATNC$^{IL4rP}$ induced tumor apoptosis more effectively than the control group or TRAIL (FIG. 8E). On the other hand, in the case of TRAIL-ATNC without a targeting peptide, the anticancer effect was insignificant (FIG. 8D). TRAIL, TRAIL-ATNC, and TRAIL-ATNC$^{IL4rP}$ did not show any change in body weight (FIG. 8C), and renal toxicity was not shown despite accumulation in the kidney for a while (BUN, Creatinine level measurement).

According to these results, there is no difference between TRAIL-ATNC and TRAIL-ATNC$^{IL4rP}$ in the apoptosis effect in vitro, but in animal experiments, it was demonstrated that attaching a targeting peptide to TRAIL-ATNC was important for tumor targeting and the anticancer effect could be determined by this.

In addition, $2\times10^6$ BxPC3-Luc cells (cancer cell growth marked by luminescence) were planted in the pancreas of 6-week-old BALB/c immunodeficient mice to create an orthotopic model. When it was thought that the size of the tumor grew adequately through BLI (Bio-luminescence intensity), they were randomly divided into 4 groups, and each of saline, and TRAIL (0.5 mg/ml), TRAIL-ATNC$^{IL4rP}$ (0.8 mg/ml) and GFP-Ferritin (0.5 mg/ml) proteins dissolved in saline, was injected at 200 µl into the tail vein of each mouse for each group. A total of 8 injections were performed once every 2 days, and the relative sizes of tumors were compared through BLI once every 3 days. Two days after the 8th injection, the last BLI of the tumor was taken, the mice were sacrificed, the tumor was harvested, and the weight of the tumor was measured.

As a result, TRAIL-ATNC$^{IL4rP}$ significantly inhibited tumor growth and decreased tumor weight compared to not only Control ($p<0.01$) but also TRAIL ($p<0.05$). Through these results, it was determined that TRAIL-ATNC$^{IL4rP}$ exhibited anticancer effects not only in the xenografted breast cancer tumor model but also in the pancreatic cancer orthotopic model in which a tumor grew in a real organ (FIG. 9).

<Example 9> Investigation of Apoptosis of TRAIL-ATNC Displaying Target Peptide

MDA-MB-231 cells were planted in each well of a 96-well plate by $5\times10^3$ cells and cultured in DMEM medium (2% FBS) at 37° C. After 24 hours, the cells were treated with each of TRAIL, TRAIL-ATNC, TRAIL-ATNC$^{IL4rP}$, and TRAIL-ATNC$^{CD44v6P}$ proteins dissolved in modified PBS (500 mM NaCl, 1 mM DTT) in half from 10 nM, and then cultured at 37° C. for 24 hours again. Thereafter, cell viability was measured using a cell number measurement kit (KLD-001, Rockland). At this time, the relative cell viability was measured when the non-protein-treated cell group was set to 100% as a control.

As a result, TRAIL-ATNC ($IC_{50}=0.11$ nM), in which TRAIL was exhibited outside the ferritin nanocage, showed about 10-fold higher cytotoxicity compared to TRAIL ($IC_{50}=1.6$ nM). TRAIL-ATNC$^{IL4rP}$ ($IC_{50}=0.48$ nM) and TRAIL-ATNC$^{CD44v6P}$ ($IC_{50}=0.36$ nM) conjugated with the target peptide showed higher cytotoxicity than TRAIL regardless of the target peptide type (FIG. 10).

<Example 10> Targeting Investigation of Target Peptides Displayed on TRAIL-ATNC

Interleukin 4 receptor (IL4R) protein was coupled to the surface of a gold sensor chip for surface resonance plasma (SPR) activated with NHS-EDC, and TRAIL-ATNC$^{IL4rP}$ dissolved in TBS was flowed from 41.67 nM to 0.65 nM in half on the IL4R-coupled gold sensor chip to analyze binding kinetics. The right channel, which was not coated with IL4R, was used as a reference.

As a result, TRAIL-ATNC$^{IL4rP}$, that is TRAIL-ATNC to which a peptide capable of binding to IL4R is attached, showed the dissociation constant ($K_D$) value of 37.67 nM for IL4R. This result indicates that the target peptide IL4rP attached to TRAIL-ATNC$^{IL4rP}$ can specifically bind to IL4R without being disturbed by TRAIL (FIG. 11).

What is claimed is:

1. A fusion polypeptide consisting of SEQ ID NO: 8.

2. A ferritin nanocage comprising the fusion polypeptide of claim 1.

3. A method of treating breast, pancreatic or liver cancer comprising administering a pharmaceutical composition comprising the ferritin nanocage of claim 2 as an active ingredient to a subject.

* * * * *

SEQUENCE LISTING

<160> NUMBER OF SEQ ID NOS: 9

<210> SEQ ID NO 1
<211> LENGTH: 168
<212> TYPE: PRT
<213> ORGANISM: Human

<400> SEQUENCE: 1

```
Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60
```

-continued

```
Glu Lys Gly Phe Tyr Tyr Ile Tyr Ser Gln Thr Tyr Phe Arg Phe Gln
65              70              75              80

Glu Glu Ile Lys Glu Asn Thr Lys Asn Asp Lys Gln Met Val Gln Tyr
                85              90              95

Ile Tyr Lys Tyr Thr Ser Tyr Pro Asp Pro Ile Leu Leu Met Lys Ser
            100             105             110

Ala Arg Asn Ser Cys Trp Ser Lys Asp Ala Glu Tyr Gly Leu Tyr Ser
            115             120             125

Ile Tyr Gln Gly Gly Ile Phe Glu Leu Lys Glu Asn Asp Arg Ile Phe
        130             135             140

Val Ser Val Thr Asn Glu His Leu Ile Asp Met Asp His Glu Ala Ser
145             150             155             160

Phe Phe Gly Ala Phe Leu Val Gly
                165
```

```
<210> SEQ ID NO 2
<211> LENGTH: 146
<212> TYPE: PRT
<213> ORGANISM: Human

<400> SEQUENCE: 2

Asp Ser Glu Ala Ala Ile Asn Arg Gln Ile Asn Leu Glu Leu Tyr Ala
1               5               10              15

Ser Tyr Val Tyr Leu Ser Met Ser Tyr Tyr Phe Asp Arg Asp Asp Val
            20              25              30

Ala Leu Lys Asn Phe Ala Lys Tyr Phe Leu His Gln Ser His Glu Glu
            35              40              45

Arg Glu His Ala Glu Lys Leu Met Lys Leu Gln Asn Gln Arg Gly Gly
        50              55              60

Arg Ile Phe Leu Gln Asp Ile Lys Lys Pro Asp Cys Asp Asp Trp Glu
65              70              75              80

Ser Gly Leu Asn Ala Met Glu Cys Ala Leu His Leu Glu Lys Asn Val
                85              90              95

Asn Gln Ser Leu Leu Glu Leu His Lys Leu Ala Thr Asp Lys Asn Asp
            100             105             110

Pro His Leu Cys Asp Phe Ile Glu Thr His Tyr Leu Asn Glu Gln Val
            115             120             125

Lys Ala Ile Lys Glu Leu Gly Asp His Val Thr Asn Leu Arg Lys Met
            130             135             140

Gly Ala
145
```

```
<210> SEQ ID NO 3
<211> LENGTH: 24
<212> TYPE: PRT
<213> ORGANISM: Artificial Sequence
<220> FEATURE:
<223> OTHER INFORMATION: Triple Helix linker

<400> SEQUENCE: 3

Glu Ala Leu Gln Gly Gln Val Gln His Leu Gln Ala Ala Phe Ser Gln
1               5               10              15

Tyr Lys Lys Val Glu Leu Phe Pro
                20
```

```
<210> SEQ ID NO 4
<211> LENGTH: 11
```

-continued

```
<212> TYPE: PRT
<213> ORGANISM: Artificial Sequence
<220> FEATURE:
<223> OTHER INFORMATION: Rigid Helix linker

<400> SEQUENCE: 4

Ala Glu Ala Ala Ala Lys Glu Ala Ala Ala Lys
1               5                   10

<210> SEQ ID NO 5
<211> LENGTH: 390
<212> TYPE: PRT
<213> ORGANISM: Artificial Sequence
<220> FEATURE:
<223> OTHER INFORMATION: fusion polypeptide

<400> SEQUENCE: 5

Met Gly Ser Ser His His His His His His Ser Ser Gly Leu Val Pro
1               5                   10                  15

Arg Gly Ser Gln His Met Val Arg Glu Arg Gly Pro Gln Arg Val Ala
                20                  25                  30

Ala His Ile Thr Gly Thr Arg Gly Arg Ser Asn Thr Leu Ser Ser Pro
            35                  40                  45

Asn Ser Lys Asn Glu Lys Ala Leu Gly Arg Lys Ile Asn Ser Trp Glu
    50                  55                  60

Ser Ser Arg Ser Gly His Ser Phe Leu Ser Asn Leu His Leu Arg Asn
65                  70                  75                  80

Gly Glu Leu Val Ile His Glu Lys Gly Phe Tyr Tyr Ile Tyr Ser Gln
                85                  90                  95

Thr Tyr Phe Arg Phe Gln Glu Glu Ile Lys Glu Asn Thr Lys Asn Asp
                100                 105                 110

Lys Gln Met Val Gln Tyr Ile Tyr Lys Tyr Thr Ser Tyr Pro Asp Pro
                115                 120                 125

Ile Leu Leu Met Lys Ser Ala Arg Asn Ser Cys Trp Ser Lys Asp Ala
    130                 135                 140

Glu Tyr Gly Leu Tyr Ser Ile Tyr Gln Gly Gly Ile Phe Glu Leu Lys
145                 150                 155                 160

Glu Asn Asp Arg Ile Phe Val Ser Val Thr Asn Glu His Leu Ile Asp
                165                 170                 175

Met Asp His Glu Ala Ser Phe Phe Gly Ala Phe Leu Val Gly Gly Ser
                180                 185                 190

Gly Gly Gly Ser Gly Glu Phe Glu Ala Leu Gln Gly Gln Val Gln His
            195                 200                 205

Leu Gln Ala Ala Phe Ser Gln Tyr Lys Lys Val Glu Leu Phe Pro Val
    210                 215                 220

Asp Gly Gly Gly Gly Ala Glu Ala Ala Ala Lys Glu Ala Ala Ala Lys
225                 230                 235                 240

Thr Ser Asp Ser Glu Ala Ala Ile Asn Arg Gln Ile Asn Leu Glu Leu
                245                 250                 255

Tyr Ala Ser Tyr Val Tyr Leu Ser Met Ser Tyr Tyr Phe Asp Arg Asp
                260                 265                 270

Asp Val Ala Leu Lys Asn Phe Ala Lys Tyr Phe Leu His Gln Ser His
                275                 280                 285

Glu Glu Arg Glu His Ala Glu Lys Leu Met Lys Leu Gln Asn Gln Arg
    290                 295                 300

Gly Gly Arg Ile Phe Leu Gln Asp Ile Lys Lys Pro Asp Cys Asp Asp
305                 310                 315                 320
```

```
Trp Glu Ser Gly Leu Asn Ala Met Glu Cys Ala Leu His Leu Glu Lys
            325             330                 335

Asn Val Asn Gln Ser Leu Leu Glu Leu His Lys Leu Ala Thr Asp Lys
            340             345                 350

Asn Asp Pro His Leu Cys Asp Phe Ile Glu Thr His Tyr Leu Asn Glu
            355             360                 365

Gln Val Lys Ala Ile Lys Glu Leu Gly Asp His Val Thr Asn Leu Arg
        370             375                 380

Lys Met Gly Ala Lys Leu
385                 390

<210> SEQ ID NO 6
<211> LENGTH: 9
<212> TYPE: PRT
<213> ORGANISM: Artificial Sequence
<220> FEATURE:
<223> OTHER INFORMATION: IL4R binding peptide

<400> SEQUENCE: 6

Cys Arg Lys Arg Leu Asp Arg Asn Cys
1               5

<210> SEQ ID NO 7
<211> LENGTH: 7
<212> TYPE: PRT
<213> ORGANISM: Artificial Sequence
<220> FEATURE:
<223> OTHER INFORMATION: MMP2 cleavage site

<400> SEQUENCE: 7

Gly Pro Leu Gly Leu Ala Gly
1               5

<210> SEQ ID NO 8
<211> LENGTH: 416
<212> TYPE: PRT
<213> ORGANISM: Artificial Sequence
<220> FEATURE:
<223> OTHER INFORMATION: fusion polypeptide

<400> SEQUENCE: 8

Met Gly Ser Ser His His His His His His Ser Ser Gly Leu Val Pro
1               5                   10                  15

Arg Gly Ser Gln His Met Val Arg Glu Arg Gly Pro Gln Arg Val Ala
            20                  25                  30

Ala His Ile Thr Gly Thr Arg Gly Arg Ser Asn Thr Leu Ser Ser Pro
        35                  40                  45

Asn Ser Lys Asn Glu Lys Ala Leu Gly Arg Lys Ile Asn Ser Trp Glu
        50                  55                  60

Ser Ser Arg Ser Gly His Ser Phe Leu Ser Asn Leu His Leu Arg Asn
65                  70                  75                  80

Gly Glu Leu Val Ile His Glu Lys Gly Phe Tyr Tyr Ile Tyr Ser Gln
            85                  90                  95

Thr Tyr Phe Arg Phe Gln Glu Glu Ile Lys Glu Asn Thr Lys Asn Asp
            100                 105                 110

Lys Gln Met Val Gln Tyr Ile Tyr Lys Tyr Thr Ser Tyr Pro Asp Pro
        115                 120                 125

Ile Leu Leu Met Lys Ser Ala Arg Asn Ser Cys Trp Ser Lys Asp Ala
        130                 135                 140
```

-continued

```
Glu Tyr Gly Leu Tyr Ser Ile Tyr Gln Gly Gly Ile Phe Glu Leu Lys
145                 150                 155                 160

Glu Asn Asp Arg Ile Phe Val Ser Val Thr Asn Glu His Leu Ile Asp
                165                 170                 175

Met Asp His Glu Ala Ser Phe Phe Gly Ala Phe Leu Val Gly Gly Ser
            180                 185                 190

Gly Gly Gly Ser Gly Glu Phe Glu Ala Leu Gln Gly Gln Val Gln His
            195                 200                 205

Leu Gln Ala Ala Phe Ser Gln Tyr Lys Lys Val Glu Leu Phe Pro Val
        210                 215                 220

Asp Gly Gly Gly Gly Ala Glu Ala Ala Ala Lys Glu Ala Ala Ala Lys
225                 230                 235                 240

Thr Ser Asp Ser Glu Ala Ala Ile Asn Arg Gln Ile Asn Leu Glu Leu
            245                 250                 255

Tyr Ala Ser Tyr Val Tyr Leu Ser Met Ser Tyr Tyr Phe Asp Arg Asp
            260                 265                 270

Asp Val Ala Leu Lys Asn Phe Ala Lys Tyr Phe Leu His Gln Ser His
        275                 280                 285

Glu Glu Arg Glu His Ala Glu Lys Leu Met Lys Leu Gln Asn Gln Arg
    290                 295                 300

Gly Gly Arg Ile Phe Leu Gln Asp Ile Lys Lys Pro Asp Cys Asp Asp
305                 310                 315                 320

Trp Glu Ser Gly Leu Asn Ala Met Glu Cys Ala Leu His Leu Glu Lys
            325                 330                 335

Asn Val Asn Gln Ser Leu Leu Glu Leu His Lys Leu Ala Thr Asp Lys
            340                 345                 350

Asn Asp Pro His Leu Cys Asp Phe Ile Glu Thr His Tyr Leu Asn Glu
        355                 360                 365

Gln Val Lys Ala Ile Lys Glu Leu Gly Asp His Val Thr Asn Leu Arg
    370                 375                 380

Lys Met Gly Ala Lys Leu Gly Gly Gly Ser Gly Gly Pro Leu Gly Leu
385                 390                 395                 400

Ala Gly Gly Gly Gly Ser Gly Cys Arg Lys Arg Leu Asp Arg Asn Cys
            405                 410                 415
```

<210> SEQ ID NO 9
<211> LENGTH: 9
<212> TYPE: PRT
<213> ORGANISM: Artificial Sequence
<220> FEATURE:
<223> OTHER INFORMATION: CD44v6P binding peptide

<400> SEQUENCE: 9

```
Cys Asn Leu Asn Thr Ile Asp Thr Cys
1               5
```